US009364616B2

(12) United States Patent
Jugl et al.

(10) Patent No.: US 9,364,616 B2
(45) Date of Patent: Jun. 14, 2016

(54) DRIVE MECHANISM OF A DRUG DELIVERY DEVICE

(75) Inventors: Michael Jugl, Frankfurt am Main (DE); Gunther Sendatzki, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 198 days.

(21) Appl. No.: 14/130,029

(22) PCT Filed: Jul. 12, 2012

(86) PCT No.: PCT/EP2012/063636
§ 371 (c)(1),
(2), (4) Date: Dec. 30, 2013

(87) PCT Pub. No.: WO2013/007769
PCT Pub. Date: Jan. 17, 2013

(65) Prior Publication Data
US 2014/0142516 A1    May 22, 2014

(30) Foreign Application Priority Data

Jul. 14, 2011    (EP) .................................... 11173935

(51) Int. Cl.
*A61M 5/315*    (2006.01)
*A61M 5/24*    (2006.01)
(52) U.S. Cl.
CPC ............. *A61M 5/31513* (2013.01); *A61M 5/24* (2013.01); *A61M 5/31525* (2013.01);
(Continued)
(58) Field of Classification Search
CPC .................... A61M 5/31541; A61M 5/31551; A61M 5/502

USPC .......................................... 604/207–209, 211
See application file for complete search history.

(56) References Cited

U.S. PATENT DOCUMENTS 4,865,591 A * 9/1989 Sams ................ A61M 5/31553
222/287
5,578,015 A * 11/1996 Robb .................... A61M 5/315
604/110

(Continued)

FOREIGN PATENT DOCUMENTS

EP          0594349      4/1994
WO      2005/021072      3/2005

(Continued)

OTHER PUBLICATIONS

International Search Report for Int. App. No. PCT/EP2012/063636, completed Nov. 30, 2012.

*Primary Examiner* — Gerald Landry, II
(74) *Attorney, Agent, or Firm* — McDonnell Boehnen Hulbert & Berghoff LLP

(57) ABSTRACT

A drive mechanism of a drug delivery device is presented comprising of a piston rod extending in an axial direction to be operably engaged with a piston of a cartridge, the piston rod being adapted to exert distally directed pressure to the piston for expelling a liquid medicament from the cartridge. A housing component to accommodates the piston rod and has a guiding member extending in a lateral plane and being engaged with piston rod for guiding the same in axial direction relative to the housing component. At least one actuation lock is used to engage with the piston rod to inhibit a proximally directed movement of the piston rod relative to the housing component.

11 Claims, 4 Drawing Sheets

(52) U.S. Cl.
CPC ...... *A61M 5/31578* (2013.01); *A61M 5/31505* (2013.01); *A61M 5/31535* (2013.01); *A61M 2005/2407* (2013.01); *A61M 2005/31506* (2013.01)

(56) References Cited

U.S. PATENT DOCUMENTS

| | | | | |
|---|---|---|---|---|
| 6,086,568 | A * | 7/2000 | Caizza | A61M 5/3234 604/110 |
| 2007/0135767 | A1 * | 6/2007 | Gillespie, III | A61M 5/2033 604/135 |
| 2008/0021389 | A1 * | 1/2008 | Runfola | A61M 5/3234 604/110 |
| 2008/0188813 | A1 * | 8/2008 | Miller | A61M 5/14566 604/189 |
| 2009/0254035 | A1 * | 10/2009 | Kohlbrenner | A61M 5/20 604/135 |
| 2009/0275916 | A1 * | 11/2009 | Harms | A61M 5/31541 604/506 |
| 2011/0245780 | A1 * | 10/2011 | Helmer | A61M 5/31515 604/211 |
| 2012/0095412 | A1 * | 4/2012 | Schabbach | A61M 5/31505 604/211 |
| 2012/0184917 | A1 * | 7/2012 | Bom | A61M 5/24 604/187 |

FOREIGN PATENT DOCUMENTS

| | | |
|---|---|---|
| WO | 2009/146996 | 12/2009 |
| WO | 2010/063687 | 6/2010 |
| WO | 2011/026931 | 3/2011 |

\* cited by examiner

DRIVE MECHANISM OF A DRUG DELIVERY DEVICE

CROSS REFERENCE TO RELATED APPLICATIONS

The present application is a U.S. National Phase Application pursuant to 35 U.S.C. §371 of International Application No. PCT/EP2012/063636 filed Jul. 12, 2012, which claims priority to European Patent Application No. 11173935.5 filed Jul. 14, 2011. The entire disclosure contents of these applications are herewith incorporated by reference into the present application.

TECHNICAL FIELD

The present invention relates to the field of drug delivery devices and in particular to injection devices, such like pen-type injectors for administering a predefined dose of a liquid medicament.

BACKGROUND

Drug delivery devices allowing for multiple dosing of a required dosage of a liquid medicament, such as liquid drugs, and further providing administration of the medicament to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

With drug delivery devices such as pen-type injectors, the medicament to be dispensed is provided in a cartridge usually comprising a vitreous body. Said body is typically sealed in proximal direction with a displaceable piston. FIG. 1 is illustrative of such a pen-type injector 10 having a drive mechanism 12 operable to exert distally directed thrust to a displaceable piston 28 of a cartridge 26 mounted therein. As shown in FIG. 1, a housing component 20 of the drive mechanism 12 comprises a radially inwardly extending guiding member or web 22 having an inner thread 24 that cooperates and mates with an external thread of a piston rod 14. The piston rod 14 is to be driven either manually or in an automated way. A rotation of the piston 14 leads to a displacement of the piston in distal direction 34. In the course of such distal displacement, a bearing disc 18 rotatably mounted on a distal bearing 16 of the piston rod 14 buts against a pressure-receiving surface of the piston 28.

Since the piston 28 is movably disposed between the sidewalls 26 of the cartridge, actuation of the piston rod 14 therefore leads to a distally directed displacement of the piston 28, thereby expelling a pre-defined amount of a liquid medicament from a distal end of the cartridge not further illustrated here. The cartridge 26 itself is accommodated in a cartridge holder 30 featuring a proximal insert piece 32, by way of which cartridge holder 30 and housing 20 can be mutually interconnected.

During a dose dispensing action, the piston 28 has to be displaced in distal direction 34 with respect to the body 26 of the cartridge. Respective counter acting or holding forces are provided by the interconnected housing components 30, 20 of the drug delivery device. Moreover, the piston 28 typically comprises an elastic rubber material, inherently exhibiting a rather slow relaxation in response to mechanical compression. After dispensing of a dose of the medicament, a non-negligible fluid pressure may therefore build up inside the body 26 of the cartridge due to an elastic relaxation of the piston and/or of a distally located piercable seal.

Furthermore, since various components of the housing 20, 30 of the drug delivery device 10 as well as of the drive mechanism 12 are manufactured of thermoplastic materials, the device and its drive mechanism may feature a certain axial play or clearance. Internal mechanical stress of various device components as well as relaxation processes of resilient or deformable components of the device and/or its cartridge may lead to a substantial pressure built up inside the cartridge, which may effectuate a post-dispensing droplet generation at the distal tip of an injection needle being in fluid communication with the inner volume of the cartridge.

The problem of such droplet generation in medical delivery devices is already addressed in WO 2009/146996 A1. There, a pressure relief mechanism is "built in" in the design of a plunger rod. Said pressure relief mechanism comprises at least one alteration in the pitch of the threads of a plunger rod arranged to interact with a number of protrusions around the inner circumferential surface in a nut for releasing the pressure exerted upon a stopper by the relative rotational movement between plunger rod and nut. Hence, when the plunger rod has rotated almost a full distance as set by a driver member, protrusions of the nut reach the end of an increased pitch of the threads of the plunger rod and fall into the sudden alteration of the pitch. Such movement causes a pressure relief of the plunger rod and therefore also a pressure relief of the content of the container.

However, such a pressure relief mechanism may increase axial clearance between drive mechanism and piston at the expense of dosing and dispensing accuracy.

Furthermore and irrespective of such a pressure relief mechanism, the general problem may arise, that due to internal pressure built up inside the cartridge and/or due to elastic relaxation of the piston or seal of the cartridge, the piston itself may exert a proximally directed pressure to the piston rod. Hence, in particular circumstances, the elastically relaxing piston of the cartridge may induce a reverse and a proximally directed displacement of the piston rod as soon as a dispensing procedure has been completed. Due to unavoidable manufacturing and assembly tolerances, such a reverse motion is disadvantageous in terms of dosing and dispensing accuracy.

Also, the mechanical components of the drive mechanism may become subject to malfunction. In fact, a proximally directed displacement of a piston rod may cause a jam of the drive mechanism and may therefore lead to severe problems for following dose setting and dispensing procedures.

It is therefore an object of the present invention to reduce or to entirely eliminate proximally directed mechanical stress acting on a piston rod of an injection device's drive mechanism. It is a further object to reduce the drive mechanisms susceptibility to errors and malfunction and to increase dosing and injection accuracy of the device. Moreover, the invention aims to improve patient safety, in particular for disposable drug delivery devices.

SUMMARY

The present invention relates to a drive mechanism of a drug delivery device. The drive mechanism comprises a piston rod of elongated shape and extending in an axial direction. The piston rod is to be operably engaged with a piston of a cartridge. In particular, the piston rod is adapted to exert distally directed pressure or thrust to the piston for expelling a predefined amount of the liquid medicament from the cartridge.

In the present context, distal direction points towards a treatment area of a patient, whereas proximal direction points in an opposite axial direction, away from the patient.

The drive mechanism further has a housing component to accommodate the piston rod. The housing component further has a guiding member extending in a lateral plane, hence, substantially perpendicular to the axial direction. The guiding member is further engaged with the piston rod in order to guide the same in axial direction relative to the housing component. Preferably, the guiding member is adapted to keep the piston rod in a pre-defined radial position relative to the housing component.

The drive mechanism further comprises at lest one actuation lock to engage with the piston rod. The actuation lock is further adapted to inhibit a proximally directed movement of the piston rod relative to the housing component. It is particularly designed to inhibit self-activated or reverse displacement of the piston rod, which may for instance evolve from elastic relaxation processes of the piston of a cartridge and/or due to mechanical stress relaxation of mutually interconnected or inter engaging housing and/or drive mechanism components of the drug delivery device.

Hence, the actuation lock serves to prevent reverse and proximally directed motion of the piston rod in response to a mechanical relaxation of the piston of the cartridge. Also, the actuation lock may provide an effective stress absorbing or stress transferring functionality. It may transfer proximally directed mechanical stress from the piston rod to the housing component, thereby relieving and/or reducing mechanical stress otherwise acting on the piston rod and/or other mechanical components of the drive mechanism operably engaged therewith.

By way of the at least one actuation lock a reverse motion of the piston rod can be effectively blocked. This is of particular benefit when the drug delivery device is designed as disposable device. With such a non-resetable drive mechanism, a replacement of an empty cartridge can be effectively prevented. At least a resetting of the drive mechanism can be made more difficult. This way, the drive mechanism or drug delivery device can even better protected against counterfeiting.

According to a preferred embodiment, the actuation lock comprises at least one distally and/or at least one radially inwardly extending stop element to engage with a recessed structure of the piston rod. The recessed structure can be designed as axial and/or radial recess in order to cooperate with the stop element, typically arranged at the guiding member of the housing component. It is of further benefit when the actuation lock comprises two mutually corresponding components provided on the outer circumference of the piston rod and on the inner circumference of the guiding member in order to provide a rotative and/or translational interlock for the piston rod relative to the housing component.

According to a preferred embodiment, the guiding member comprises multiple stop elements arranged along the circumference of the piston rod. Preferably, the multiplicity of stop elements is equidistantly arranged around the piston rod's circumference. This way, proximally directed mechanical stress acting on the piston rod can be smoothly deflected towards the housing component via the actuation lock and the guiding member.

According to a further preferred aspect, the at least one stop element comprises a resiliently deformable spring element. The spring element may be resiliently deformed or bended in the course of a distally directed displacement of the piston, e.g. during a dose dispending procedure. By way of the elastic or resiliently deformable spring element the dispending procedure is only minimally affected. The at least one stop element is resiliently deformable when the piston rod is subject to a distally directed displacement during a dose dispensing action. However, in the opposite direction, the stop element provides a rather stiff and inflexible mechanical stop adapted to absorb and/or to transfer mechanical stress to the housing component via the guiding member.

In a further preferred aspect, the guiding member or web and the piston rod are threadedly engaged. Typically, the guiding member comprises a central and threaded through opening to threadedly receive and to guide the piston rod. It is further of advantage, when the guiding member is integrally formed with the housing component. Preferably, guiding member and housing component are manufactured as injection molded thermoplastic components. By way of the threaded engagement, a distally directed displacement of the piston rod relative to the housing component or relative to the guiding member is always accompanied by a rotative movement of said piston rod.

In a preferred aspect, the piston rod further comprises an outer thread to cooperate with an inner thread of the guiding member. The piston rod also comprises multiple grooves extending along the circumference of the piston rod. Such grooves have a pitch that differs from the pitch of the outer thread. Typically, the grooves extend at a lower pitch compared to the pitch of the outer thread.

It is even conceivable that the grooves extend substantially perpendicular to the extension of the piston rod. Moreover, the grooves may co-align in axial direction and may be present only at a particular lateral side face of the piston rod. Preferably, the piston rod comprises multiple axially extending rows of grooves adapted to co-operate and to engage with stop elements correspondingly arranged at the guiding member.

The slope or pitch of the groove typically matches and corresponds with the number, position and mechanical properties of the co-operating stop elements.

According to a further preferred embodiment, multiple stop elements are arranged along the circumference of a distal end of the inner thread of the guiding member. Such stop elements preferably extend in distal direction and further project radially inwardly. It is due to such an inwardly directed displacement that the stop elements latch with corresponding grooves of the piston rod. Preferably, when the stop elements comprise resiliently deformable or pivotable spring elements, they may radially outwardly deform or pivot against the action of a respective spring force. This way, also with arbitrary relative axial positions of piston rod and housing component, a sufficient proximally directed blocking of the piston rod can be provided.

Moreover, since the multiple stop elements are arranged along the circumference at or of a distal end of the inner thread, the threaded engagement of piston rod and guiding member may almost remain entirely unaffected by the actuation lock.

Furthermore, it is conceivable that the stop elements are integrally formed with the guiding member. The stop elements may comprise bendable or pivotable flaps attached to the guiding member along a perforated or structurally weakened area, allowing and supporting a respective pivoting motion of the stop element with respect to the guiding member. Alternatively, the stop elements may be designed as separate pieces to be assembled in respective and co-operating receptacles provided in or at the guiding member. Especially, when designed as separate pieces, the stop elements may comprise a metal piece or component made of metal.

According to another preferred aspect, the piston rod comprises at least one radially inwardly extending recess or several radially inwardly extending recesses to mate with corresponding radially inwardly extending stop elements. Hence, the stop elements of the actuation lock may not only provide a blocking device to impede axially and proximally directed displacement of the piston rod relative to the housing component. Additionally, by way of radially inwardly extending recesses co-operating with corresponding stop elements, also a rotational interlock or a rotational stop feature can be provided in general. In embodiments, where the piston rod is threadedly engaged with the guiding member, such rotational interlock may already be sufficient to establish an actuation lock adapted to prevent proximally directed motion of the piston rod relative to the housing component.

In a further embodiment, the recesses of the piston rod comprise a radially inwardly extending stop face to engage with a lateral side edge of the corresponding stop element. Adjacent to the stop face, the radially inwardly extending recess typically comprises a bevelled or slanted shape continuously adapting and approaching the over-all circular cross section, outer shape or circumference of the piston rod.

Moreover and according to another preferred aspect, the stop element may also engage with the piston rod with a lower side edge facing in distal direction. The lower side edge of the stop element is predominately adapted to engage with a circumferentially extending outer groove of the piston rod.

Apart from the described drive mechanism the invention further relates to a drug delivery device and in particular to a pen-type injector, preferably of disposable type, which is adapted for setting and dispensing a dose of a medicament. The drug delivery device comprises a drive mechanism as described above and further has a cartridge holder to accommodate a cartridge being at least partially filled with a medicament to be dispensed by the drug delivery device.

The cartridge holder is preferably adapted to directly interconnect with the housing component of the drive mechanism that accommodates and receives the piston rod. The cartridge holder further serves to keep the cartridge in place with respect to the housing components of the drug delivery device, such that distally directed thrust can be precisely exerted on the piston of the cartridge.

In particular embodiments, wherein the drug delivery device is designed as a disposable device, a pre-filled cartridge is readily arranged inside the drug delivery device. Upon completion of an assembly process, the drug delivery device is generally ready for use. When the medicament provided in the cartridge is consumed or used up, the disposable device is intended to be discarded. The actuation lock of the drive mechanism serves to prevent and to reset the drive mechanism once the piston rod has reached a distal end position. This way, misuse of the device, e.g. disassembling of cartridge holder and housing component for the purpose of replacing an empty cartridge by a filled one, are no longer successful and the drug delivery device may therefore provide an improved mechanism against counterfeiting.

It is to be noted here, that all features, beneficial effects and aspects mentioned in connection with the drive mechanism are also valid and transferable to a respected drug delivery device.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—

(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

```
H-(Lys)4-des Pro36, des Pro37 Exendin-
4(1-39)-NH2,

H-(Lys)5-des Pro36, des Pro37 Exendin-
4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39),
``` wherein the group -Lys6-NH2 may be bound to the C-terminus of the Exendin-4 derivative;
or an Exendin-4 derivative of the sequence

```
H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2,
```

H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in detail by making reference to the drawings in which.

DETAILED DESCRIPTION

Figure 1:
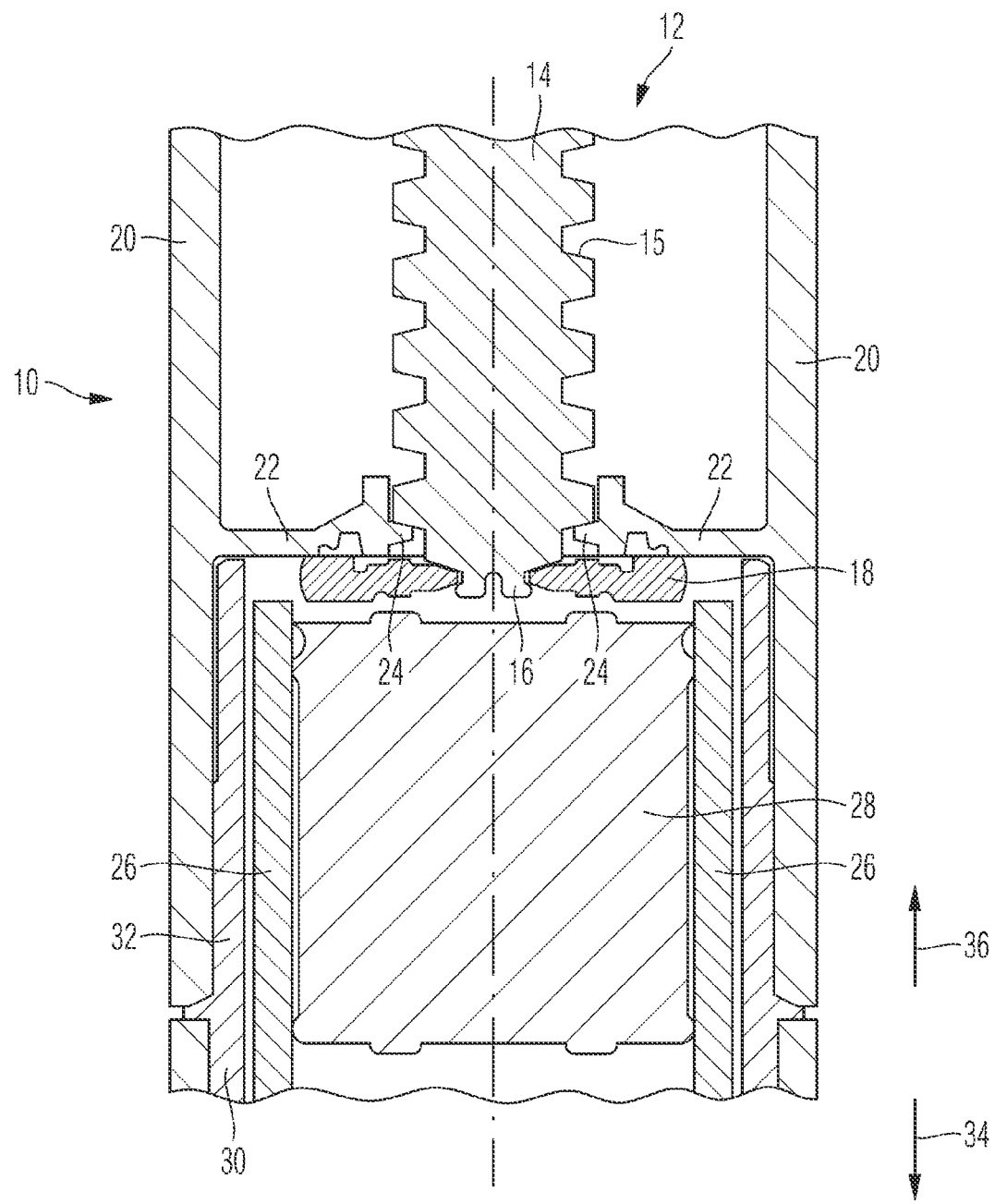
FIG. 1 shows a cross-sectional view of the distal portion of a drive mechanism of a pen-type injector according to the prior art.
Figure 2:
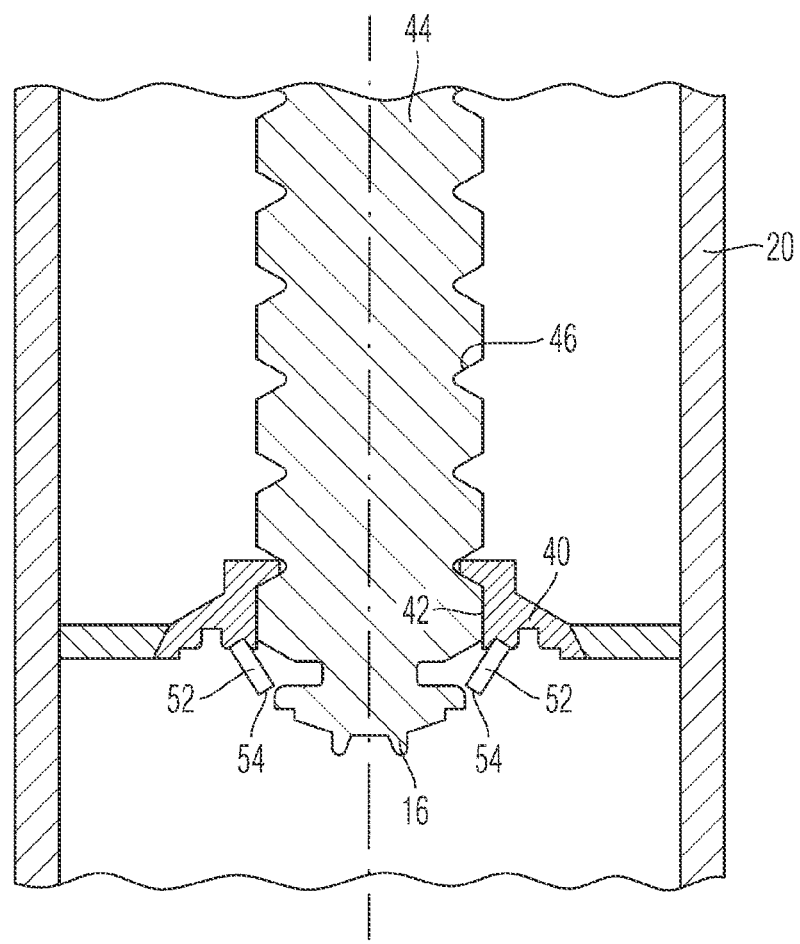
FIG. 2 shows a cross section of a modified drive mechanism having an actuation lock, FIG. 3 exemplary shows a modified piston rod in a perspective view.
Figure 3:
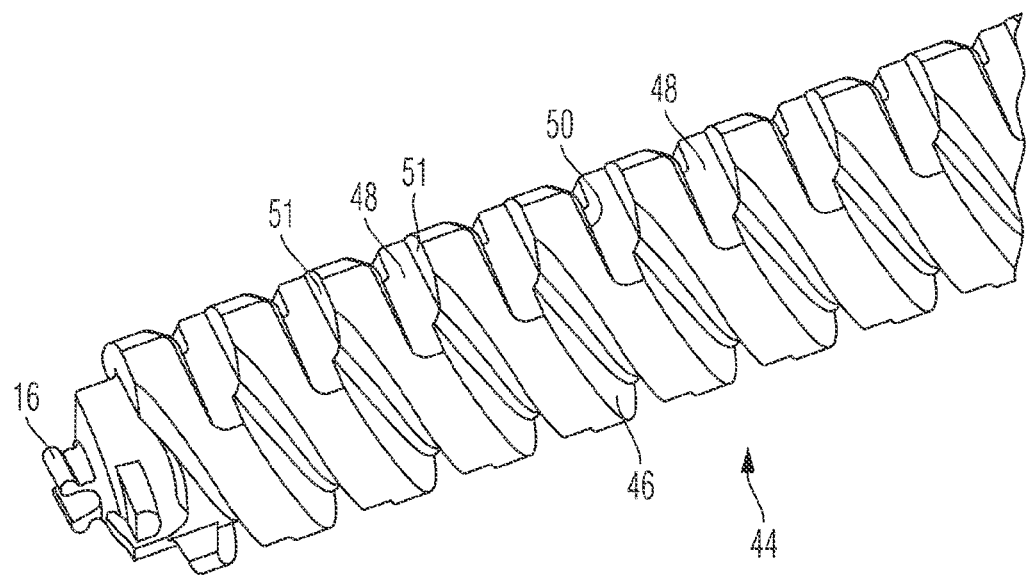

In FIGS. 2 and 3, a modified piston rod 44 threadedly engaged with a guiding member or web 40 is illustrated. The guiding member 40 is arranged inside a proximal portion of a housing 20 of a drug delivery device and further has a central through opening comprising an inner thread 42 that co-operates with a corresponding outer thread 46 of the piston rod. By rotating the piston rod 44 in circumferential direction, axial position of the piston rod 44 with respect to the housing component 20 can be modified. Preferably, by turning the piston rod 44 in a clockwise sense, the piston rod 44 advances in distal direction 34, thereby exerting pressure or mechanical stress to a piston 28 of a cartridge 26 as indicated in FIG. 1.

The actuation lock of the present invention comprises one or several stop elements 52 extending at a lower or distal end face of the guiding member 40 in a tilted or slanted configuration, such that the distally located or lower edge 54 of the stop elements 52 extends in distal direction as well as radially inwardly, thereby engaging with a recessed structure 48 of the piston rod 44 as illustrated in FIG. 3. Hence, the piston rod not only comprises a helically wound outer thread 46 but also has various grooves 48 intersecting the thread 46 and comprising a different pitch compared to the thread.

Moreover, the recessed structure 48 comprises distally located edges 50 and proximally located edges 51, wherein the distally located edges 50 are adapted to engage with the lower or distal edge 54 of the stop elements 52, as indicated in FIG. 2. The proximally located edge 51 may comprise a somewhat bevelled or slanted surface for not hindering a distally directed movement of the piston rod 44 relative to the housing component 20.

By the illustrated actuation lock provided by grooves 48 and mutually corresponding stop elements 52, any proximally directed mechanical stress acting on the piston rod can be effectively and directly transferred to the circumferential housing component 20 via the guiding member 40, that may be integrally formed with the tubular housing 20. This way, a jamming of the drive mechanism due to mechanical stress acting on the piston rod in proximal direction can be effectively prevented. Also, disadvantageous effects of inevitable axial clearance on the dosing and dispensing accuracy can be reduced.

Figure 4:
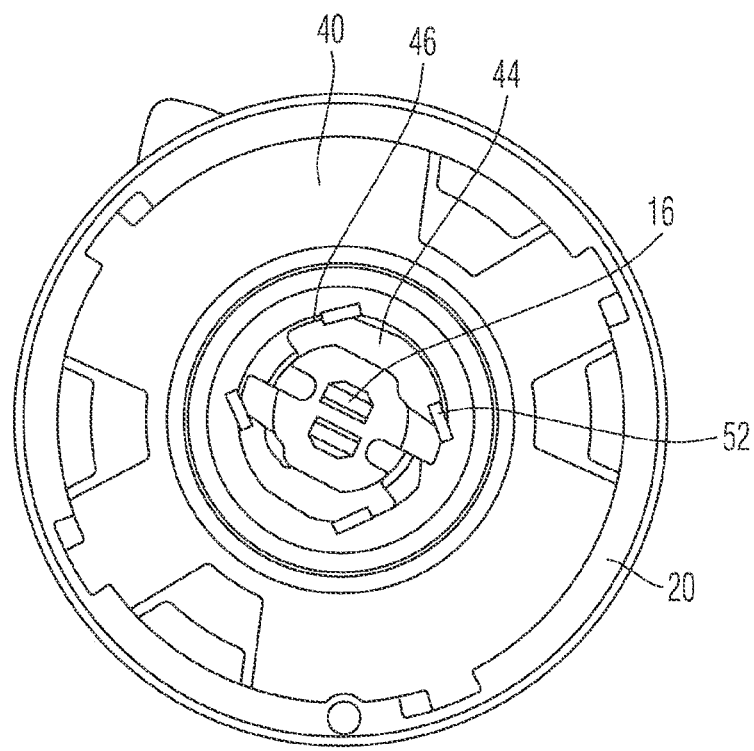
FIG. 4 shows a bottom view of a piston rod engaged with a surrounding guiding member.
Figure 5:
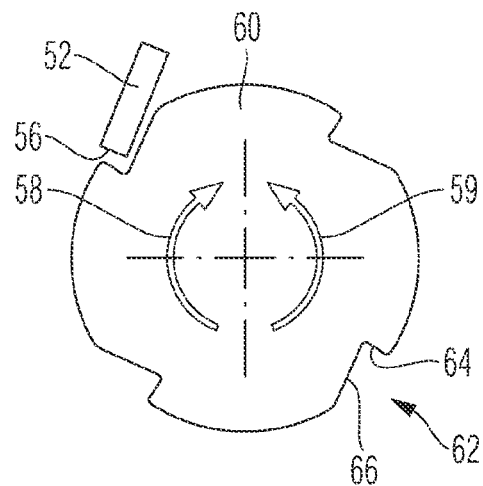
FIG. 5 shows a schematic illustration of a rotational interlock and FIG. 6 is illustrative of a circumferentially toothed piston rod according to the present invention.

While the embodiment according to FIGS. 2 and 3 particularly relates to a direct axially acting mutual abutment of stop elements 52 and piston rod 44, the embodiment as illustrated in FIGS. 4 and 5 provides a rotational actuation lock as described below. As shown in FIG. 5, the piston rod 60 comprises four regularly arranged laterally and/or radially inwardly extending recesses 62, each of which having a rather steep stop face 64 facing in clockwise direction 58 in the illustration according to FIG. 5.

Adjacent to the rather steep edge 64, the recess 62 comprises a somewhat bended or arched portion 66. As indicated in FIG. 5, the lateral sidewall portion 56 of the stop element 52 may engage with the stop face 64 of the recess 62 in order to inhibit a clockwise directed motion 58 of the piston rod 60. A rotation along the opposite direction, hence counter clockwise as indicated by the arrow 59 is possible since the stop face 64 separates from the lateral stop face 56 of the stop element 52. Such clockwise rotation is typically accompanied with a distally directed displacement of the piston rod 60 relative to a housing 20.

With the embodiment according to FIGS. 2 and 3 as well as with the embodiment following FIGS. 4 and 5, it is beneficial, when the stop elements 52 are biased towards a center region. Hence, a bending or pivoting of the free end or of an engaging edge 54, 56 of the stop elements 52 typically occurs against a spring force or of a comparable restoring force.

By way of the rotational interlock as shown in the embodiment according to FIGS. 4 and 5 a proximally directed displacement of the piston rod 44 relative to the housing 20 can be effectively prevented due to a threaded engagement of piston rod 60 and stop elements 52.

Figure 6:
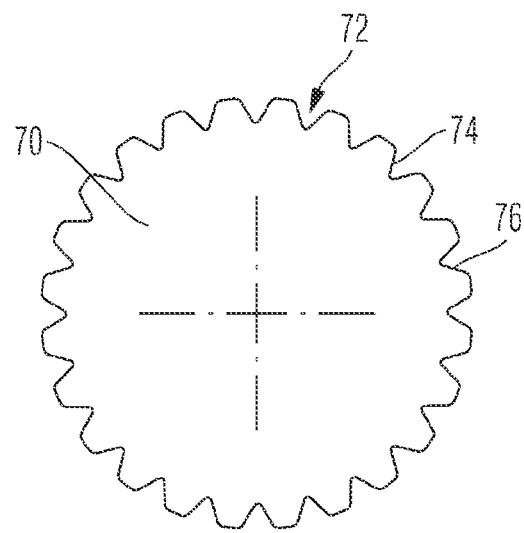

The embodiment as further illustrated in FIG. 6 refers to a piston rod 70 comprising a toothed circumferential structure. Said structure has numerous recesses 42 featuring oppositely oriented leading and trailing edges 74, 76. With this particular embodiment it is further benefit, when the slope of the edge 74 differs from the slope of the edge 76 in order to provide a unidirectional rotative interlock with stop elements 52 arranged at a housing of the drug deliver device.

The invention claimed is:

1. A drive mechanism of a drug delivery device, comprising:
   a piston rod extending in an axial direction to be operably engaged with a piston of a cartridge, the piston rod being adapted to exert distally directed pressure to the piston for expelling a liquid medicament from the cartridge,
   a housing component to accommodate the piston rod and having a guiding member extending in a lateral plane and being engaged with the piston rod for guiding the piston rod in the axial direction relative to the housing component, wherein the piston rod comprises an outer thread, and the guiding member and the piston rod are threadedly engaged such that the piston rod is rotatably supported in the housing component, and
   at least one actuation lock to engage with the piston rod to inhibit a proximally directed movement of the piston rod relative to the housing component,
   wherein the piston rod further comprises at least one radially inwardly extending recess to mate with at least one radially inwardly extending stop element of the actuation lock, and
   wherein the guiding member comprises multiple stop elements arranged along the circumference of the piston rod.

2. The drive mechanism according to claim 1, wherein the actuation lock comprises at least one distally and/or radially inwardly extending stop element to engage with a recessed structure of the piston rod.

3. The drive mechanism according to claim 2, wherein the at least one stop element comprises a resiliently deformable spring element.

4. The drive mechanism according to claim 1, wherein the piston rod comprises multiple grooves extending along the circumference of the piston rod having a pitch that differs from the pitch of the outer thread.

5. The drive mechanism according to claim 4, wherein the grooves extend substantially perpendicular to the extension of the piston rod.

6. The drive mechanism according to claim 4, wherein multiple stop elements are arranged along the circumference of a distal end of the inner thread of the guiding member and extend in distal direction radially inwardly.

7. The drive mechanism according to claim 4, wherein the stop elements are integrally formed with the guiding member.

8. The drive mechanism according to claim 1, wherein the recesses comprise a radially inwardly extending stop face to engage with a lateral side edge of the stop element.

9. The drive mechanism according to claim 1, wherein the stop element engages with the piston rod with a lower side edge facing in distal direction.

10. A drug delivery device for setting and dispensing a dose of a medicament comprising:
    a drive mechanism according to claim 1, and
    a cartridge holder to accommodate a cartridge filled with a medicament to be dispensed.

11. The drug delivery device according to claim 10 comprising a cartridge at least partially filled with a medicament.

* * * * *